United States Patent [19]

Shiplee, III

[11] 4,333,479
[45] Jun. 8, 1982

[54] DISPOSABLE NEEDLE ASSEMBLY

[76] Inventor: Lewis D. Shiplee, III, 1112 S. Magnolia Dr., Apt. V-204, Tallahassee, Fla. 32301

[21] Appl. No.: 80,484

[22] Filed: Oct. 1, 1979

[51] Int. Cl.³ .............................................. A61B 5/14
[52] U.S. Cl. ................................................. 128/766
[58] Field of Search .............. 128/764, 766, 221, 274; 251/7

[56] References Cited

U.S. PATENT DOCUMENTS

| | | | |
|---|---|---|---|
| 1,124,285 | 1/1915 | Brown | 128/766 |
| 1,766,918 | 6/1930 | Meyer | 128/766 |
| 2,197,995 | 4/1940 | Crowley | 251/7 |
| 2,471,623 | 5/1949 | Hubbell | 251/7 X |
| 2,518,165 | 8/1950 | Millard | 128/766 |
| 2,655,152 | 10/1953 | Turner et al. | 128/766 |
| 3,143,109 | 8/1964 | Gewertz | 128/766 |
| 3,181,529 | 5/1965 | Wilburn | 128/766 |
| 3,262,448 | 7/1966 | Ring et al. | 128/221 X |
| 3,297,558 | 1/1967 | Hillquist | 251/7 X |
| 3,304,934 | 2/1967 | Bautista | 128/766 |
| 3,308,809 | 3/1967 | Cohen | 128/766 |
| 3,491,748 | 1/1970 | Pate | 128/766 |
| 3,557,778 | 1/1971 | Hughes | 128/766 |
| 3,616,789 | 11/1971 | Grabhorn | 128/766 |
| 3,734,080 | 5/1973 | Petterson et al. | 128/766 |
| 3,817,240 | 6/1974 | Ayres | 128/766 |
| 3,848,579 | 11/1974 | Villa-Real | 128/766 |
| 3,882,899 | 5/1975 | Ginsberg et al. | 251/7 X |
| 3,886,930 | 6/1975 | Ryan | 128/766 |
| 4,036,232 | 7/1977 | Genese | 128/278 |
| 4,106,497 | 8/1978 | Percarpio | 128/766 |
| 4,140,108 | 2/1979 | Nugent | 128/766 |
| 4,215,702 | 8/1980 | Ayer | 128/766 |
| 4,280,509 | 7/1981 | Bethkenhagen et al. | 128/764 X |

FOREIGN PATENT DOCUMENTS

| | | | |
|---|---|---|---|
| 1288383 | 6/1962 | France | 128/766 |
| 1586087 | 2/1970 | France | 128/766 |
| 469055 | 2/1952 | Italy | 128/766 |

*Primary Examiner*—John D. Yasko
*Attorney, Agent, or Firm*—Roger L. Martin

[57] ABSTRACT

A disposable blood drawing device has an evacuated container and holder therefor as well as a dual needle assembly which is connectable to the holder. The assembly has an elongated housing with opposite end openings in which hypodermic and tap needles are respectively mounted and internally interconnected by a resilient tube that is compressable against one of the opposite walls of the housing by means of a push button which is manipulated exterially to compress and thus limit the flow through the resilient tube. The push button has a lateral stop element that will pass through an opening for receiving the push button during the assembly of the assembly but which engages the internal surface of one wall of the housing to prevent withdrawal of the button. The mounting for the tap needle carries an adaptor for connecting the device with the holder.

7 Claims, 9 Drawing Figures

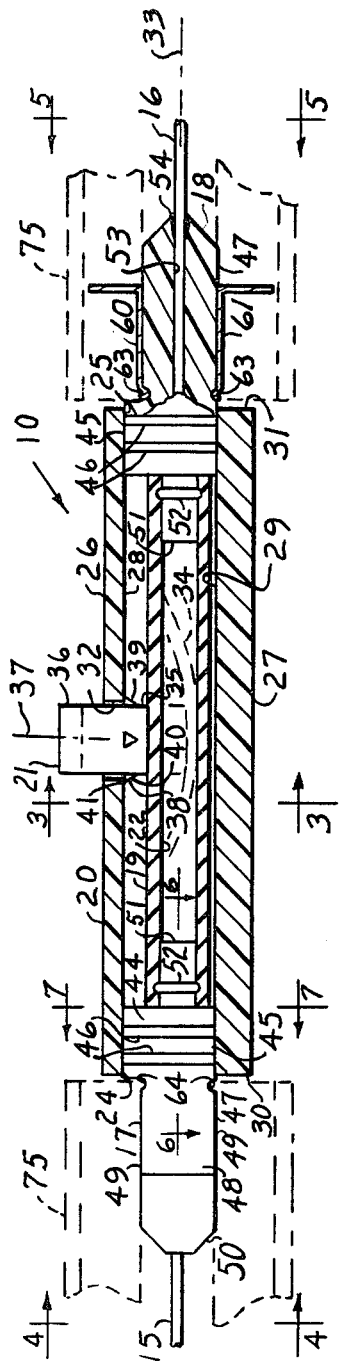
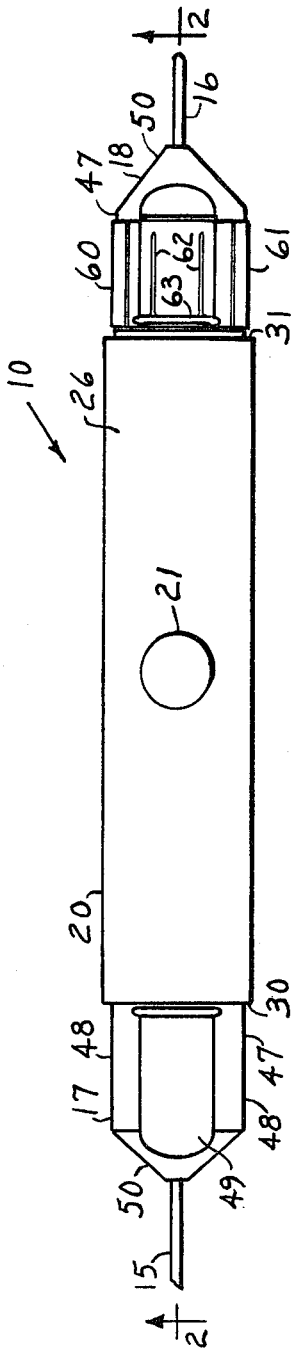

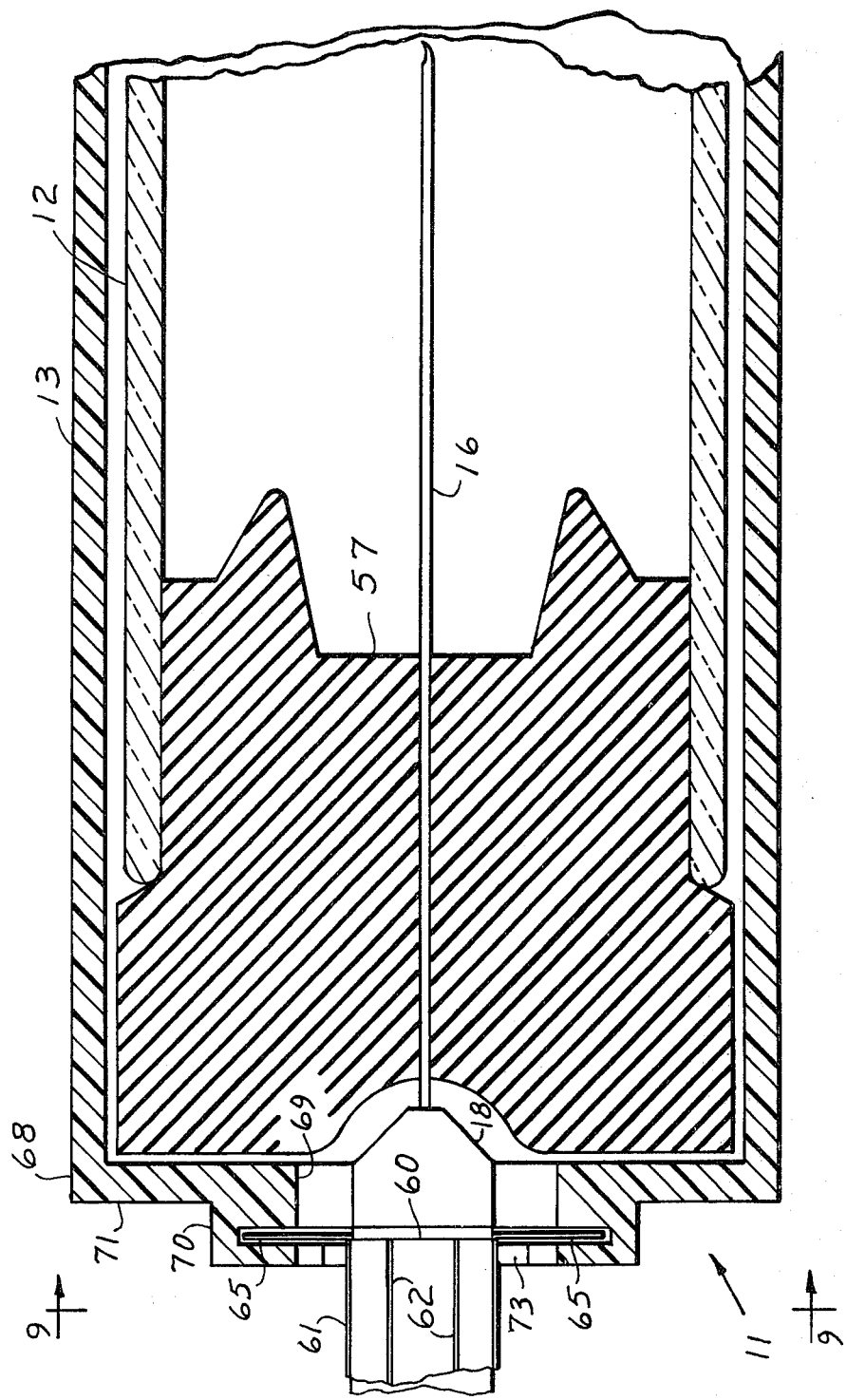
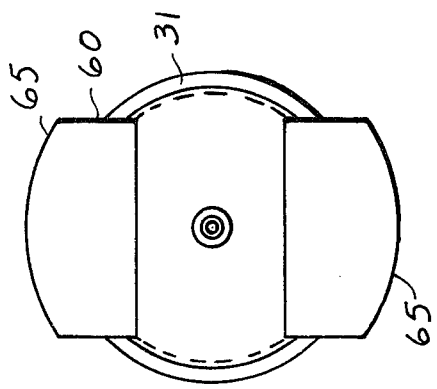

DISPOSABLE NEEDLE ASSEMBLY

BACKGROUND OF THE INVENTION

The art of drawing blood from patients for testing purposes has in recent years centered around the use of blood drawing devices that utilize pre-evacuated containers or tubes in which the blood tests are actually carried out. These devices normally include a dual needle assembly which includes a hypodermic needle and a tap needle which is used for tapping the evacuated container. To facilitate the taking of multiple samples, such devices also include a holder for the evacuated containers. In use the holder is coupled to the needle assembly and serves as a holder for the container during the blood drawing process as well as a structure for guiding the tap needle and container stopper into a vacuum tapping relation at which the needle has penetrated the stopper and is in communication with the sterile contents of the vessel.

Certain problems are encountered in using pre-evacuated containers. For one, the blood withdrawals are sometimes so rapid as to cause collapse of the patient's vein. This is undesirable because the need then arises to seek out another vein to collect the blood specimen and with all the well known patient trauma that is associated with the use of hypodermic needles. Yet another problem which is encountered is that of mechanical hemolysis caused by a shearing action on blood cells that transpires with rapid movement of the blood through the assembly components. Such hemolysis results in unsatisfactory specimens that must be discarded and again secured from the patient.

The vein collapsing problems can be generally overcome by providing a suitable valve mechanism between the hypodermic needle and the evacuated container. This permits the hospital technician or other attendant to regulate the flow of blood under the action of the partial vacuum in the sterile container to a rate which avoids collapsing of the patient's vein. This flow regulation also tends to minimize mechanical hemolysis but a further avoidance of the problem results from the use of streamlined flow structures in the mounts for and at the proximal ends of the needles.

Various different types of valve arrangements have been advocated and used in the dual needle assemblies. Many have involved the use of complicated structures which are too expensive to utilize in disposable items. Others have parts that can be accidentally disassembled during use of the devices. This, of course, requires the technician to start over again with a new sterile assembly and under circumstances which frequently follow an initial penetration of patient tissue by the hypodermic needle. Yet other valve arrangement require the use of both hands in order to manipulate the valve, and under circumstances where it would be preferable to have one hand free to perform other tasks.

The need accordingly exists for an inexpensive needle assembly of the kind contemplated in which the parts are reliably coupled together and protected from disassembly during use and in which the blood flow can be easily and effectively regulated by the technician.

A general object of the invention is to provide improvements in blood drawing devices. One particular object is to provide improvements in dual needle assemblies that are used with evacuated containers in blood drawing devices. Still another object is to provide a needle assembly of the kind contemplated and wherein the blood flow may be regulated by the attendant by a simple means for constricting the passage through a resilient tube. Other objects of the invention are to provide a simple, inexpensive means for regulating the flow of blood between the needles of a dual needle assembly and which during the process of manufacturing the disposable item, can be readily assembled by the workers. Other objects will be evident hereinafter.

STATEMENT OF THE INVENTION

The inventor provides a disposable dual needle assembly in which the proximal ends of the hypodermic and tap needles are connected by a resilient tube structure that is housed in a housing which is equipped with an exteriorally manipulatable push button that is used for constricting the passage through the tube to thus limit the blood flow through the assembly to the evacuated container. The arrangement provided protects the tube from being disconnected from the needle mounts yet simultaneously permits the valving action to be accomplished by a simple compression of the tube through finger manipulation of the push button. In accord with certain aspects of the invention, the housing is a simple extrusion which is provided with opposite end openings in which the needles are mounted. Between the openings, the extrusion is equipped with opposite side walls, one being equipped with an opening for the push button that is manipulated at the exterior of the housing while the other provides an interior surface against which the tube is compressed. In accord with other aspects of the invention, the push button is equipped with a lateral stop arrangement that permits it to be forced through the lateral opening during the assembly of the device but which in the final assembly engages an interior surface of the side wall to prevent withdrawal of the button from the housing. Other aspects of the invention have to do with a housing in which the interior surfaces of the opposite side walls are non-symmetrically located in reference to the center axis of the housing so as to provide a close physical relation between the tube and wall against which it is compressed by the push button and to also provide an arrangement that tends to minimize the excursion required of the push button to effectuate tube compression.

In the preferred embodiment, the needles of the disposable needle assembly are mounted at their proximal ends in mounting members which are press fit in the end openings of the housing and provided with outer portions that may be equipped with a means for attaching the needle assembly to the container holder. The mounting member is adapted at its inner end to receive the end of the tube. The mounting member, of course, has a bore or channel in which the needle is mounted and at the proximal end of the needle, the mounting member is equipped with a contoured enlargement that aids in reducing mechanical hemolysis during use of the device.

BRIEF DESCRIPTION OF THE DRAWINGS

The novel features which are believed to be characteristic of this invention are set forth with particularity in the appended claims. The invention, itself, however, both as to its organization and method of operation, together with further objects and advantages thereof, may best be understood by reference to the following description taken in connection with the accompanying drawings, wherein:

FIG. 1 is a top plan view of a disposable dual needle assembly embodying the principles of the invention;

FIG. 2 is a longitudinal sectional view in elevation taken generally along the Lines 2—2 of FIG. 1;

FIG. 5 is an end elevational view at the vacuum tap needle end of the assembly as generally seen along the Lines 5—5 of FIG. 2;

FIG. 8 is a longitudinal section at the vacuum tap end of the needle assembly illustrating its operating relation to an evacuated container and holder therefor, the container and holder being shown in section.

DESCRIPTION OF PREFERRED EMBODIMENT

Figure 9:
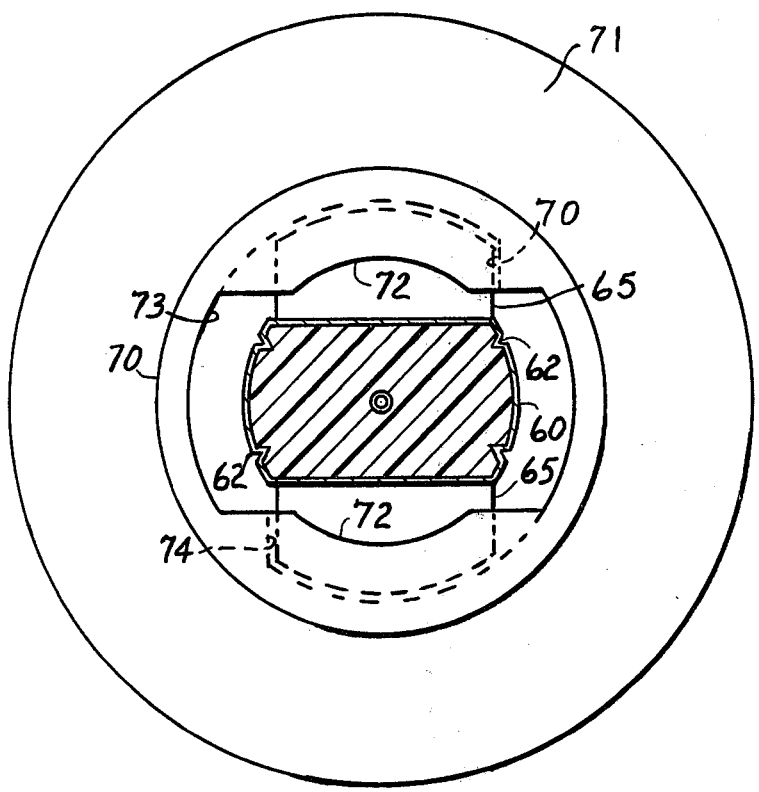
FIG. 9 is a transverse section taken generally along the Lines 9—9 of FIG. 8.
Figure 7:
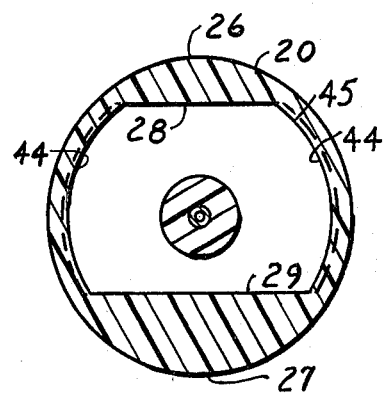
FIG. 7 is a transverse section taken generally along the Lines 7—7 of FIG. 2.
Figure 3:
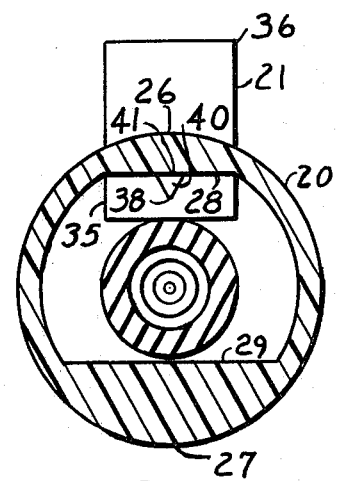
FIG. 3 is a transverse sectional view taken generally along the Lines 3—3 of FIG. 2.
Figure 6:
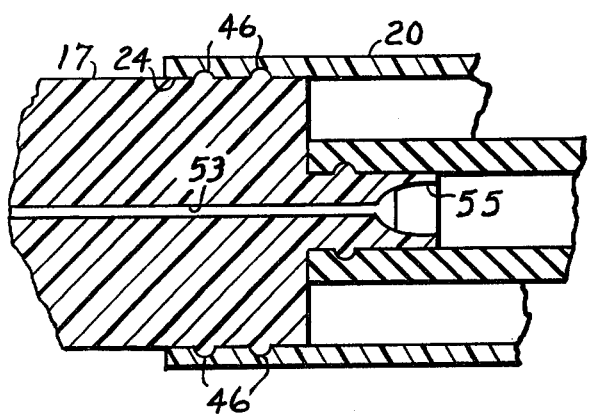
FIG. 6 is a horizontal section through a fragment of the assembly as seen along the Lines 6—6 of FIG. 2.
Figure 4:
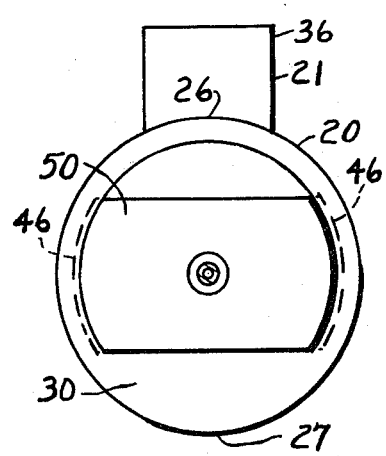
FIG. 4 is an end elevational view at the hypodermic needle end of the assembly as taken generally along the Lines 4—4 of FIG. 2, with certain parts in section.

Reference is now made to the drawings and wherein a disposable dual needle assembly embodying the invention is generally designated at 10. The assembly 10 serves as a component of a disposable blood drawing device 11 (FIG. 8) that in addition to the needle assembly 11, includes an evacuated container 12 which has a sterile interior that is under a partial vacuum and a holder component 13 in which the container 12 is held. Holder 13 serves to hold the container 12 when its vacuum is being tapped and it also serves in guiding the tap needle and container into a vacuum tapping relation seen in FIG. 8.

The needle assembly 10 includes a hollow hypodermic needle 15, a hollow vacuum tap needle 16, a pair of needle mounting members 17 and 18, an elongated, resilient tube 19 which interconnects the needles, and an elongated housing 20 which is equipped with a push button 21 for constricting the tube passage 22 so as to limit the blood flow through the assembly 10.

The housing 20 is an elongated, cylindrical member which is preferably extruded from a suitable thermoplastic material. The housing 20 has opposite end openings 24 and 25 in which the needles 15 and 16 are mounted by means of members 17 and 18. The housing 20 is equipped with opposite side walls 26 and 27 which extend between the opposite end openings 24 and 25. Between the opposite ends 30 and 31 of the housing, the top side wall 26 is equipped with a lateral opening 32 in which the button 21 for regulating the blood flow is mounted.

In the interior of housing 20, side walls 26 and 27 have planar surfaces 28 and 29 respectively and which are offset from the center axis 33 of the housing 20 and arranged in parallel. The bottom side wall surface 29 is offset from the axis 33 by a distance which is slightly greater than the radius of tube 19 so that in the assembly 10, the excursion requirement for the push button 21 to accomplish obstruction of the tube passage 22 is minimal. The top wall surface 28, on the other hand, is offset from the center axis 33 by a distance which is greater than that of the bottom wall surface 29 so as to accommodate the location of the inner end 35 of push button 21.

Push button 21 is a generally cylindrical element that is preferably made from a somewhat resilient plastic material so as to permit deformation of the stop discussed below during the assembly of the component. Button 21 is mounted in the lateral opening 32 of housing 20 and as arranged, the push button 21 is mounted for substantially linear movement in the opening 32 along an axis 37 which is normal to the center axis 33 of the housing. Push button 21 can be moved inwardly to pinch or compress the tube, as into the position shown at 34, by exerting finger pressure against the outer end 36 of the button. As this happens, the inner end 35 of the button moves inwardly and compresses the tube 19 against the inner surface of the bottom side wall 27 to thereby constrict the passage 22.

At its inner end 35, the push button 21 is equipped with a pair of lateral projections 38 and 39 which are arranged at the opposite sides of the button so as to serve as stop elements in limiting outward movement of the button. The button snuggly fits in the lateral opening 32 and the projections or protuberances 38 and 39 are each equipped with an inclined side surface 40 as well as another surface 41 that lies in a plane normal to the button axis 37. The arrangement of the inclined surface 40 is such as to permit the button to be inserted in the opening 32 from the housing exterior during the assembly of the components of assembly 10 and to a point at which the projections 38 and 39 pass through the opening 32 to a location in the interior of the housing. At this point in the assembly of the device 10, the button more or less snaps into place. Thereafter the protuberances 38 and 39 serve as stop elements that prevent the withdrawal of the button 21 from the opening because outward button movement causes the upper surfaces 41 of the projections 38 and 39 to engage the inner surface 28 of wall 26 and thus stop further outward movement of the button.

The needle mounting members 17 and 18 are identical in structure. Each member has a central portion 45 which generally conforms in shape to that of the end openings 24 and 25. The arcuate side walls 44 of the central portion 45 is equipped with a pair of side ribs 46 that provide a tight fit between the parts when the mount is press fit in the appropriate end opening of the housing. These needle mounting members also have an outer portion 47 which is equipped with a pair of opposite arcuate side walls 48 and a pair of opposite planar side walls 49. These walls 48 and 49 merge with a conical end wall 50 at the outer extremity of the member and which as seen in the drawings, converges upon the center axis 33. The needle mounts also have a cylindrical inner portion 51 which is adapted to fit in one of the opposite end openings 56 of tube 19. The inner portion 51 is provided with a circular rib 52 so as to again provide a tight fit when the tube is press fit onto the inner portion 51.

Each needle mount 17 and 18 also has a bore 53 for receiving the needle and which is coaxially arranged in the assembly 10 with the axis 33 of housing 20. At the outer end extremity of the needle mounting member, the bore 53 is flared to receive a suitable adhesive 54 which serves to fix the needle in the mount. The needle, of course, is received in the bore during the assembly of the device 10 and at its proximal end, each needle is flared and located in a streamlined enlargement 55 of the bore 53 and which serves to minimize the shear of blood cells as the blood leaves or enters the needles during use of the device.

The outer portion 47 of the tap needle mount 18 is equipped with a coupling 60 for releasably securing the assembly 10 to a holder 13 for the evacuated container 12. Coupling 60 includes a sleeve portion 61 which is adapted and arranged to fit on the outer portion 47 of member 18 and is crimped to the outer portion 47 by longitudinally extending crimps 62 and transverse crimps 63 that fit in transverse grooves 64 at the base of the planar side walls 49. The coupling 60 also has a pair of radially projecting flanges 65 at the opposite side walls 49 (FIG. 5) and which are used in coupling the assembly to the container holder 13.

FIGS. 8 and 9 best illustrate the arrangement for coupling assembly 10 to the evacuated container holder 13. Holder 13 has an open outer end (not shown) in which the evacuated container 13 is inserted in the process of using the device 11. At its base end 68, the holder 13 has an end wall 71 with a small central opening 69 that accommodates reception of the end extremity of the outer portion 47 of the vacuum tap needle mounting member 18 (FIG. 8). At its exterior, end wall 71 has an annular section 70 which is integrally formed with the end wall and which is provided at its outer extremity with a pair of diametrically opposite and radially inwardly projecting flanges 72. Flanges 72 are so spaced apart as to accommodate reception of the coupling flanges 65 therebetween in the process of coupling the assembly 10 to the holder 13.

When the radial flanges 65 of coupling 60 are received in the center opening 73 of annular section 70, rotation of assembly 10 a quarter turn rotates the flanges 65 to positions between the flanges 72 and the end wall 71 of holder 13. Here the flanges 65 become seated against integral stop portion 74 when the assembly 10 is coupled to the holder 13. Obviously the holder 13 and assembly 10 are disconnected by a clockwise quarter rotation (see FIG. 9) of assembly 10 relative to the holder 13 followed by axial movement of the components away from each other.

The dual needle assembly 10 is, of course, sterilized and to maintain sterile conditions, suitable caps 75 that fit on the outer portions 47 of the mounts 17 and 18 are provided to house the needles. These caps are, of course, removed to use the disposable assembly 10.

In normal use, the cap covering the hypodermic needle 15 is first removed and the assembly 10 is manipulated to penetrate and locate the end of the needle in the patient's blood vein. Thereafter, in the normal process of using the assembly, the cap covering the tap needle 16 end of the assembly is next removed and the container holder 13 is coupled to the assembly in the manner described in the consideration of FIGS. 8 and 9. As the holder is being attached to the assembly 10, the push button 21 may be pressed inwardly to close the passage 22 of tube 19 so as to prevent a flow of blood through the assembly under the blood pressure condition encountered in the patient's vein. Thereafter, and with the passage 22 closed off by the technician's finger pressure on button 21, the technician manipulates the stopper end of the evacuated container 12 into the holder 13 and to a point at which the stopper 57 is penetrated by the tap needle 16 and communicates with the evacuated interior of the container 12.

The arrangement of the tube 19 is, of course, such that the opposite ends of the passage communicate with the hollows of the needles. As such, when needle 16 penetrates the stopper 57 with the button depressed, a partial vacuum is created in the tube 19 up to the point at which the depressed button closes off the passage at the pinched position designated at 34. Thereafter the technician may gradually release the pressure on button 21 to regulate the flow of blood from the vein through needle 15, tube 19 and thence through tap needle 16 to the interior of container 12. As soon as the specimen is taken, of course, container 12 may be removed from holder 13 to take yet another blood specimen, all without the need for removing the assembly 11 from the patient's arm. During the exchange of containers, the technician may maintain button 21 at the depressed state that closes off the passage 22 to again prevent blood flow under the pressure conditions encountered in the patient's veins.

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

What is claimed as new and what it is desired to secure by Letters Patent of the United States is:

1. In a disposable blood drawing device comprising an evacuated container having a stopper, a holder for the container, and a dual needle assembly that is connectable with the holder for receiving and delivering blood to an evacuated container held thereby, the improved dual needle assembly comprising a housing having opposite end openings, a hypodermic needle mounted in one of said end openings for penetrating and receiving blood from a blood vein, a tap needle mounted in the other of said end openings for penetrating the stopper and delivering the received blood to a container held by the holder, a resilient tube located in the interior of the housing and having a passage that interconnects and communicates with the hypodermic and tap needles for conveying the received blood to the tap needle, and a substantially linearly movable push button that is mounted in the housing and manipulatable at the exterior thereof to constrict said passage and thereby limit the flow of blood therethrough.

2. In a disposable blood drawing device comprising an evacuated container having a stopper, a holder for the container, and a dual needle assembly that is connectable with the holder for receiving and delivering blood to an evacuated container held thereby, the improved dual needle assembly in accord with claim 1, wherein said housing has opposite lateral side walls and a lateral opening that communicates with the interior of the housing through one of said side walls, and wherein said push button extends through and is substantially linearly movable in the lateral opening to compress said tube and close said passage.

3. In a disposable blood drawing device comprising an evacuated container having a stopper, a holder for the container, and a dual needle assembly that is connectable with the holder for receiving and delivering blood to an evacuated container held thereby, the improved dual needle assembly in accord with claim 2 wherein said push button has stop means located in the interior of said housing and arranged to engage said one of said side walls and thereby limit outward movement thereof.

4. In a disposable blood drawing device comprising an evacuated container having a stopper, a holder for the container, and a dual needle assembly that is connectable with the holder for receiving and delivering blood to an evacuated container held thereby, the improved dual needle assembly comprising a housing having opposite end openings, a hypodermic needle mounted in one of said end openings for penetrating and receiving blood from a blood vein, a tap needle mounted in the other of said end openings for penetrating the stopper and delivering the received blood to a container held by the holder, a resilient tube located in the interior of the housing and having a passage that interconnects and communicates with the hypodermic and tap needles for conveying the received blood to the tap needle, and a push button that is mounted in the housing and manipulatable at the exterior thereof to constrict said passage and thereby limit the flow of blood therethrough, said housing having opposite lateral side walls and a lateral opening that communicates with the interior of the housing through one of said side walls, said push button being arranged to extend through said lateral opening and being movable therein to compress said tube and close said passage, said push button having stop means located in the interior of said housing and arranged to engage said one of said side walls and thereby limit outward movement thereof, and said stop means having an inclined surface.

5. In a disposable blood drawing device comprising an evacuated container having a stopper, a holder for the container, and a dual needle assembly that is connectable with the holder for receiving and delivering blood to an evacuated container held thereby, the improved dual needle assembly comprising a housing having opposite end openings, a hypodermic needle mounted in one of said end openings for penetrating and receiving blood from a blood vein, a tap needle mounted in the other of said end openings for penetrating the stopper and delivering the received blood to a container held by the holder, a resilient tube located in the interior of the housing and having a passage that interconnects and communicates with the hypodermic and tap needles for conveying the received blood to the tap needle, and a push button that is mounted in the housing and manipulatable at the exterior thereof to constrict said passage and thereby limit the flow of blood therethrough, said housing having opposite lateral side walls and a lateral opening that communicates with the interior of the housing through one of said side walls, said push button being arranged to extend through said lateral opening and being movable therein to compress said tube and close said passage, and said housing having a center axis, each of said lateral side walls having a planar interior surface that is offset from said axis, the planar interior surface of said one of said side walls being further offset radially from said axis than the planar interior surface of the other of said side walls, and said push button being arranged to compress said tube against the planar interior surface of the other of said side walls.

6. In a disposable blood drawing device comprising an evacuated container having a stopper, a holder for the container, and a dual needle assembly that is connectable with the holder for receiving and delivering blood to an evacuated container held thereby, the improvement in accord with claim 1 wherein the improved dual needle assembly further comprises a pair of needle mounting members which are press fit in the respective end openings of said housing and which house the proximal ends of the hypodermic needle and tap needle respectively, wherein each of said mounting members has an inner portion which is received in the tube passage, and wherein the mounting member for the tap needle is equipped with a means for coupling the assembly to the holder.

7. In a disposable blood drawing device comprising an evacuated container having a stopper, a holder for the container, and a dual needle assembly that is connectable with the holder for receiving and delivering blood to an evacuated container held thereby, the improvement comprising a housing having opposite end openings, a hypodermic needle mounted in one of said end openings for penetrating and receiving blood from a blood vein, a tap needle mounted in the other of said end openings for penetrating the stopper and delivering the received blood to a container held by the holder, a resilient tube located in the interior of the housing and having a passage that interconnects and communicates with the hypodermic and tap needles for conveying the received blood to the tap needle, and a push button that is mounted in the housing and manipulatable at the exterior thereof to constrict said passage and thereby limit the flow of blood therethrough, said assembly further comprising a pair of needle mounting members which are press fit in the respective end openings of said housing and house the proximal ends of the hypodermic needle and tap needle respectively, each of said mounting members having an inner portion which is received in the tube passage, the mounting member for the tap needle being equipped with a means for coupling the assembly to the holder, said housing having opposite lateral side walls and a lateral opening that communicates with the interior of the housing through one of said side walls, said push button being arranged to extend through said lateral opening and being inwardly movable therein to compress said tube and close said passage, said housing having a center axis and each of said side walls having a planar interior surface that is offset from said axis, the planar interior surface of said one of said side walls being further offset radially from said axis than the planar interior surface of the other of said side walls, said push button having stop means located in the interior of said housing and arranged to engage said one of said side walls and thereby limit outward movement of the push button, and said stop means having an inclined surface that facilitates the insertion of said push button into said lateral opening.

* * * * *

UNITED STATES PATENT AND TRADEMARK OFFICE
CERTIFICATE OF CORRECTION

PATENT NO. : 4,333,479
DATED : June 8, 1982
INVENTOR(S) : Lewis D. Shiplee, III, It is certified that error appears in the above—identified patent and that said Letters Patent is hereby corrected as shown below:

On the title page [76] Inventor: should read,

Lewis D. Shiplee, III
    1504 Wekewa Nene
    Tallahassee, Fla. 32301

Signed and Sealed this

Seventh Day of September 1982

[SEAL]

Attest:

GERALD J. MOSSINGHOFF

Attesting Officer     Commissioner of Patents and Trademarks